United States Patent
Kennedy et al.

(10) Patent No.: US 6,200,589 B1
(45) Date of Patent: *Mar. 13, 2001

(54) BIOLOGICAL IMPLANTS OF SEMIPERMEABLE AMPHIPHILIC MEMBRANES

(75) Inventors: Joseph P. Kennedy; Shahram Shamlou, both of Akron; Richard P. Levy, Canton, all of OH (US)

(73) Assignee: The University of Akron, Akron, OH (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/032,316

(22) Filed: Feb. 27, 1998

Related U.S. Application Data

(63) Continuation of application No. 08/710,206, filed on Sep. 13, 1996, now abandoned.

(51) Int. Cl.[7] .............. A61K 9/50; A61K 47/32; A61L 31/00
(52) U.S. Cl. .......... 424/424; 424/487; 424/486; 435/180
(58) Field of Search .................... 424/484, 501; 435/180

(56) References Cited

U.S. PATENT DOCUMENTS

| | | | |
|---|---|---|---|
| 4,298,002 | 11/1981 | Ronel et al. | 128/260 |
| 4,353,888 | 10/1982 | Sefton | 424/25 |
| 4,402,694 | 9/1983 | Ash et al. | 604/891 |
| 4,892,538 | 1/1990 | Aebischer et al. | 604/891.1 |
| 4,942,204 | 7/1990 | Kennedy et al. | 525/293 |
| 5,073,381 | 12/1991 | Ivan et al. | 424/487 |
| 5,292,515 | 3/1994 | Moro et al. | |
| 5,387,237 | 2/1995 | Fournier et al. | 623/11 |
| 5,554,147 | 9/1996 | Batich et al. | 604/892.1 |
| 5,800,828 | 9/1998 | Dionne et al. | |
| 5,807,944 | * 9/1998 | Hirt et al. | 526/279 |
| 5,834,001 | 10/1998 | Dionne et al. | |
| 5,869,077 | 2/1999 | Dionne et al. | |
| 5,874,099 | 2/1999 | Dionne et al. | |

FOREIGN PATENT DOCUMENTS

| | | |
|---|---|---|
| 3942116 A1 | 6/1991 | (DE). |
| 01266103 | * 10/1989 | (JP). |

OTHER PUBLICATIONS

"Maintenance of Normogylcemia in Diabetic Mice by Subcutaneous Xenografts of Encapsulated Islets" by Lacy et al., Science Journal, vol. 254, pp. 1782–1784, Sep. 27, 1991.

"Application of AN69 Hydrogel to Islet Encapsulation: Evaluation in the Streptozotocin–Induced Diabetic Rat Model" by Prevost et al. Transplantation Proceedings, vol. 27, No. 6, pp. 3393–3395, Dec. 1995.

"Novel Synthetic Membranes for Immunoisolation of Islet Cells" by Shamlou et al., Abstract Only, Jun., 1996 poster presentation.

(List continued on next page.)

*Primary Examiner*—Peter F. Kulkosky
(74) *Attorney, Agent, or Firm*—Renner, Kenner, Greive, Bobak, Taylor & Weber

(57) ABSTRACT

An implantable biological device including a semipermeable membrane formed into a geometric shape capable of encapsulating biological cells and capable of immunoisolating the biological cells upon introduction into the body, the semipermeable membrane including an amphiphilic copolymer network having hydrophobic segments and hydrophilic segments, wherein the hydrophobic segments include polyolefins terminated with radicals selected from the group consisting of acryloyl groups, methacryloyl groups and mixtures thereof and wherein the hydrophilic segments include polyacrylates. Also provided is a method of encapsulating and immunoisolating cells using the semipermeable membrane and method of treating ailments using the implantable biological device.

22 Claims, 3 Drawing Sheets

OTHER PUBLICATIONS

"Amphiphilic networks: II. Biocompatibility and Controlled Drug Release of Poly[isobutylene–co–2(dimethylamino)ethyl methacrylate]" by Chen et al., *Journal of Biomedical Materials Research*, vol. 23, 1327–1342 (1989).

"Tailoring Polymers for Biological Uses" by J.P. Kennedy. S. Shamlou et al J. of Biomed. Materials Res., vol. 35 157–163 (1997).*

* cited by examiner

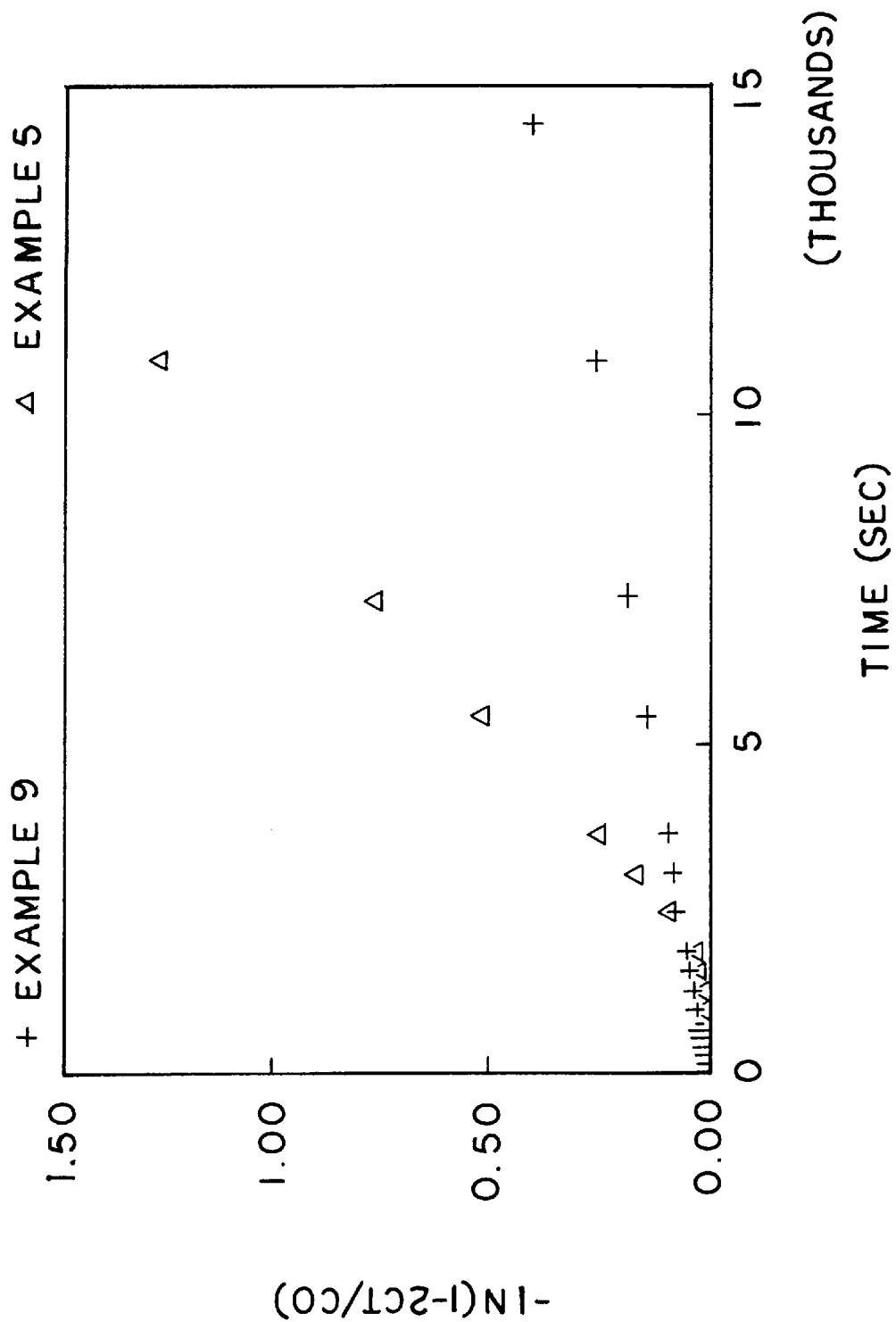

BIOLOGICAL IMPLANTS OF SEMIPERMEABLE AMPHIPHILIC MEMBRANES

This application is a continuation of U.S. Ser. No. 08/710,206, filed on Sep. 13, 1996, now abandoned.

This invention was made with government support under a grant from the National Science Foundation. The government may have certain rights to the invention.

TECHNICAL FIELD

The present invention generally relates to implantable biological devices. More particularly, the present invention relates to biological devices that can encase cells and selectively regulate the passage of biological material in and out of the device. Specifically, the device is a geometric structure of a polymeric amphiphilic network having encased therein biological cells.

BACKGROUND OF THE INVENTION

Graft rejection of biological cells, organs, devices and the like that are placed into living organisms severely limits many medical treatments. For example, pancreatic transplantation, which is the only treatment of Type I diabetes that is capable of consistently inducing insulin independence and normalizing blood glucose is severely limited by graft rejection and the need for toxic immunosuppression.

One theory advanced to overcome the limitation caused by graft rejection is to place pancreatic islets in an immuno protected device that would allow the diffusion of insulin generated by the islet cells. Heretofore in the art, the term immunoisolation has been used to describe the state of being protected from immune rejection by enclosure within a membrane. It has been advanced that semipermeable membranes would be highly desirous for this task.

Semipermeable membranes are known. For example, Kennedy et al. in U.S. Pat. Nos. 4,942,204 and 5,073,381 teach amphiphilic networks that are employed as pharmaceutical carries capable of controlled drug release. More specifically, the amphiphilic networks are copolymeric compositions having hydrophobic and hydrophilic segments. Although these networks are synthesized for controlled drug release devices, implants for enzyme immobilization, artificial arteries, blood-contacting applications, and various implantable reservoirs for drugs and metabolites for veterinary and human applications, the amphiphilic networks taught therein are not synthesized to prevent the diffusion of molecules, and moreover, prevent the diffusion of molecules having a certain molecular weight while allowing the diffusion of molecules of a different molecular weight. In other words, a need still exists to synthesize and employ a semipermeable membrane to create an implantable device capable of immunoisolating cells.

SUMMARY OF INVENTION

It is therefore, an object of the present invention to provide implantable biological devices that immunoisolate foreign biological matter.

It is another object of the present invention to provide implantable biological devices that are biocompatible and hemocompatible.

It is yet another object of the present invention to provide implantable biological devices that can encase biological matter or cells and selectively regulate the passage of biological material in and out of the device.

It is another object of the present invention to provide implantable biological devices that can be implanted in the body by employing a relatively non-invasive medical procedure.

It is still another object to provide a method for the treatment of diabetes by providing to a diabetic an implantable biological device having encased therein pancreatic islets that are immunoisolated.

At least one or more of the foregoing objects, together with the advantages thereof over the known art relating to implantable biological devices, which shall become apparent from the specification which follows, are accomplished by the invention as hereinafter described and claimed.

In general the present invention provides a biological device comprising a semipermeable membrane formed into a geometric shape capable of encapsulating biological cells and capable of immunoisolating the biological cells upon introduction into the body, the semipermeable membrane comprising an amphiphilic copolymer network having hydrophobic segments and hydrophilic segments, wherein the hydrophobic segments include polyolefins capped with radicals selected from the group consisting of acryloyl groups, methacryloyl groups and mixtures thereof and wherein the hydrophilic segments include polyacrylates derived from an acrylate selected from the group consisting of formulas (II), (III) and (IV)

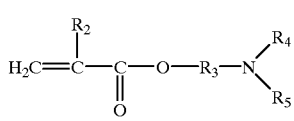

(II)

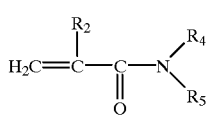

(III)

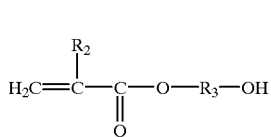

(IV)

where $R_2$ is hydrogen or methyl, $R_3$ is an alkylene group having from about 2 to about 4 carbon atoms, and $R_4$ and $R_5$ may be the same or different and selected from the group consisting of hydrogen and an alkyl radicals having from 1 to about 4 carbon atoms.

The present invention also includes a method for a method of treating diabetes comprising the step of implanting in a living organism at least one biocompatible device having encased therein pancreatic islet cells, the device comprising a semipermeable membrane formed into a geometric structure that encases and immunoisolates the islet cells, wherein the semipermeable membrane is a amphiphilic copolymer network having hydrophobic segments and hydrophilic segments, the hydrophobic segments including polyolefins capped with radicals selected from the group consisting of acryloyl groups, methacryloyl groups and mixtures thereof and the hydrophilic segments include polyacrylates derived from an acrylate selected from the group consisting of formulas (II), (III) and (IV)

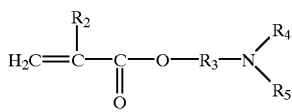

(II)

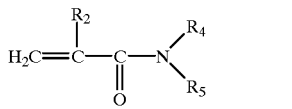

(III)

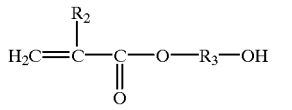

(IV)

where $R_2$ is hydrogen or methyl, $R_3$ is an alkylene group of about 2 to about 4 carbon atoms, and $R_4$ and $R_5$ may be the same or different and each is hydrogen or an alkyl radical of 1 to about 4 carbon atoms.

The present invention further includes a method of encapsulating and immunoisolating cells using a semipermeable membrane comprising an amphiphilic copolymer network having hydrophobic segments and hydrophilic segments, wherein the hydrophobic segments include polyolefins capped with radicals selected from the group consisting of acryloyl groups, methacryloyl groups and mixtures thereof and wherein the hydrophilic segments include polyacrylates derived from an acrylate selected from the group consisting of formulas (II), (III) and (IV)

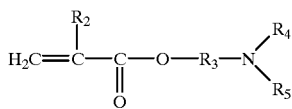

(II)

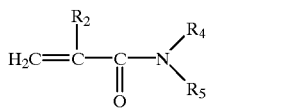

(III)

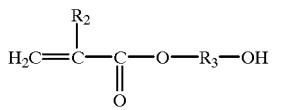

(IV)

where $R_2$ is hydrogen or methyl, $R_3$ is an alkylene group having from about 2 to about 4 carbon atoms, and $R_4$ and $R_5$ may be the same or different and selected from the group consisting of hydrogen and an alkyl radicals having from 1 to about 4 carbon atoms; and wherein the semipermeable membrane is impermeable to molecules having a molecular weight greater than about 50,000.

BRIEF DESCRIPTION OF THE DRAWINGS

FIG. 4 is a linear plot of the raw data of FIG. 3.

PREFERRED EMBODIMENT FOR CARRYING OUT THE INVENTION

Figure 1:
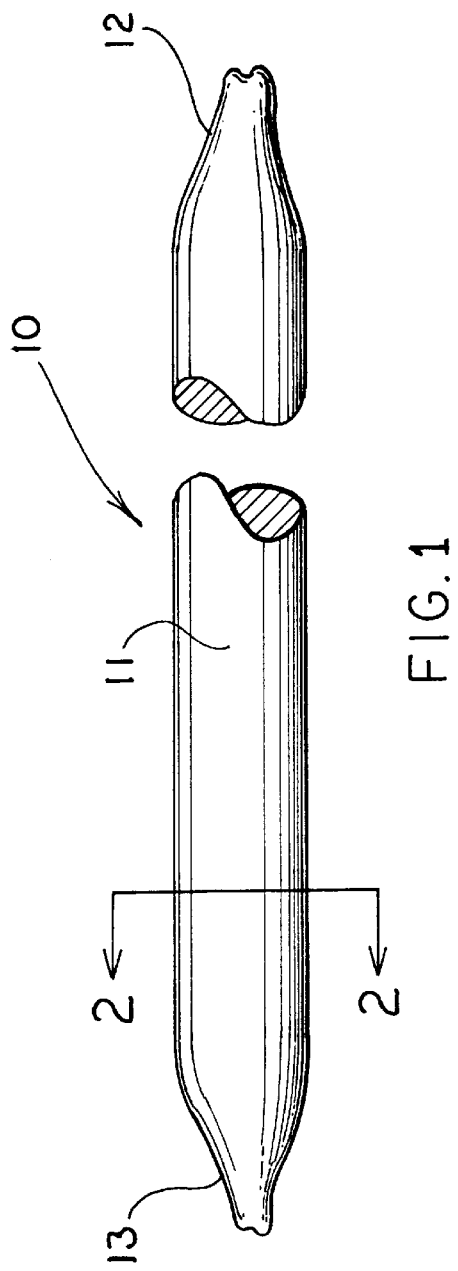
FIG. 1 is a fragmented side view of a cylindrical biological device.

The present invention is generally directed toward implantable biological devices. The biological devices of the present invention are capable of immunoisolating cells and other biological matter that can be encased therein. This characteristic of the biological devices of the present invention derives primarily from the unique membrane employed in creating the biological device. Although the cells and biological matter encased within the implantable devices are stored in a state of immunoisolation, the unique membrane employed allows the encased cells to impact the physiological environment in which the biological device is implanted by selectively regulating the flow of biological matter in and out of the device.

For purposes of this disclosure, the term immunoisolate will refer to the act of protecting, by immunoisolation, cells and other biological matter from the immune system of the host. In other words, upon implantation of the biological device into the body of a patient, the ability of the biological device to immunoisolate the contents thereof protects such contents from undergoing attach by cells, antibodies and the like of the patients various defense mechanisms.

Reference above has been made to cells or biological matter that can be encased within the biological devices of the present invention. The preferred embodiments of the present invention are directed to devices having cells encased therein, and therefore reference to cells will be used hereinafter. Nonetheless, it should be appreciated that other biological matter, such as metabolites, can be encased within the devices of the present invention. Reference to these materials, however, should not be construed as limiting the biological device of the present invention inasmuch as there are a broad range of medical treatments that can employ the device. It is also believed that with the technology of the present invention, those skilled in the art will find new ways of employing the biological device of the present invention for various medical applications.

The biological device of the present invention is created from a semipermeable amphiphilic membrane. The membrane is both biocompatible and hemocompatible. Specifically, the membrane is a cocontinuous crosslinked copolymeric three-dimensional network having hydrophobic and hydrophilic segments. Due to the thermoset nature of the semipermeable membranes employed, the membranes are formed by cast polymerization. Synthesis of the semipermeable membranes employed in creating the biological devices of the present invention will be described in greater detail hereinafter.

In order for the biological device of the present invention to encase cells for purposes of immunoisolation, the semipermeable membrane employed in creating the biological devices is typically formed into a geometric structure. The structure, therefore, includes a reservoir having some particular volume. It should be appreciated that the reservoir is completely surrounded by the semipermeable membrane such that the only way any matter can pass in or out of the reservoir is through the membrane.

Although any size, shape or configuration of the present invention can be employed, it is preferred that the size, shape and configuration be such that will allow as non-invasive a medical procedure as possible to implant the device. In the preferred embodiment of the present invention the geometric structure comprises a cylindrical structure having the ends thereof pinched so as to seal the reservoir, which is formed by the inner volume of the cylinder. With reference to FIG.

Figure 2:
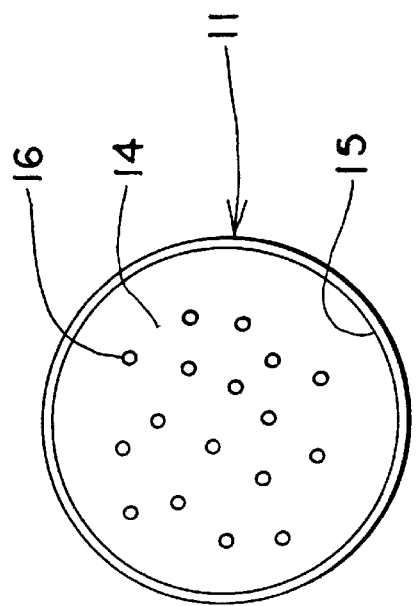
FIG. 2 is a is a cross-sectional view of a cylindrical biological device having cells therein.

1, the preferred biological device of the present invention 10 is shown, which is comprised of the semipermeable membrane 11, disclosed herein. The ends 12 and 13 are pinched to seal the inner reservoir. Referring then to FIG. 2, the reservoir 14 is shown within the semipermeable membrane 11 having an inner diameter 15. Cells 16, such as pancreatic islets, are encased therein.

The size of the device is primarily a function of the desired volume of the reservoir, although the reservoir can be as large as medically necessary or as small as technologically possible. In the preferred embodiment where pancreatic islets are encased within the reservoir, the volume required is a function of the amount of islet cells required. Typically, a volume of less than about 0.12 ml per 100,000 islet cells is necessary. This cell to volume ratio is preferred as it is believed that such ratio allows sufficient area for the cells to react with various reagents in the physiological medium in which the device is placed. Other ranges, of course, can be employed.

In the preferred embodiment, the reservoir volume is typically less than about 1 ml, preferable less than about 0.5 ml and most preferably less than about 0.1 ml. When a cylindrically shaped device is employed, these volume ranges can be achieved with a wide variety of length and diameter dimensions, as the thickness of the membranes employed are typically in the range from about 0.001 to about 0.1 cm thick, preferably from about 0.003 to about 0.08 cm thick, and more preferably from about 0.005 to about 0.02 cm thick. Thus, the length of the cylindrical devices is generally less than about 20 cm long, preferably less than about 10 cm long, and most preferably in the range from about 2 to about 5 cm long. To achieve the desired reservoir volume, one of ordinary skill in the art, without undue experimentation or calculation, can then readily determine the diameter size required. With the goal of providing for a non-invasive medical procedure to implant the devices, the diameters are typically less than about 3 mm, preferably less than about 2 mm, and most preferably less than about 1 mm.

Those skilled in the art, without undue experimentation, can form such structures using the cast polymerization techniques taught herein. For example, a sheet of the semipermeable membrane of the present invention can be formed into a pouch by using cyano acrylate as an adhesive. Further, a tube can be formed by causing the copolymerization of the semipermeable membrane to take place within a larger rotating tube, the centrifugal force experienced during copolymerization causing the copolymer to form around the inner diameter of the rotating tube. The ends of the tube can be sealed using cyano acrylate as an adhesive.

With respect to the medical treatments in which the biological devices of the present invention can be employed, the range of treatments is broad as indicated above. The primary use of the device, however, is to immunoisolate the contents thereof and yet allow for diffusion of molecules in and out of the device. The ability to allow the diffusion of certain molecules in and out of the device is important because activators or stimulators need to enter the device and react or simply effect secretion or synthesis by the cell of some desired product such as hormones or chemical agents utilized by or affecting the body. The secreted or synthesized cell material must then be able to diffuse out of the device and enter the physiological environment in which the device is implanted.

For example, with reference to the preferred embodiment wherein the device carries pancreatic islets, glucose must enter the device and bind with the islet cells. The cells then produce insulin that must be able to diffuse out of the device. Other examples include treating chronic pain by encasing within the biological device of the present invention cells that produce dopamines in response to certain stimuli. Another example includes treating hemophilia.

With respect to the preferred embodiment of the present invention where pancreatic islets are encased within the device, it is generally desirable to create a network where glucose and/or insulin can permeate the membrane at a rate of at least $1 \times 10^7$ cm$^2$/s, preferably $5 \times 10^{-7}$ cm$^2$/s, and more preferably $1 \times 10^{-6}$ cm$^2$/s.

It has been found that in remedying or reversing diabetes, about 700,000 to about 1 million islet cells are sufficient to reverse diabetes. This determination is generally based on the assumption that about 10,000 cells per kilogram of body weight is desirable. Accordingly, treatment of diabetes using the device or devices of the present invention should achieve this level either by completely providing the appropriate amount of cells to provide insulin to the entire body or providing an amount of cells sufficient to supplement the patients active cells.

Regarding treatment using the biological devices of the present invention, implantation by non-evasive procedure is preferred. A non-evasive procedure generally refers to a procedure that creates minimal pain, discomfort and recovery time to the patient. For example, given the relatively small size of the preferred devices of the present invention, a minimal incision is required to implant the device. It is further envisioned that a very narrow cylindrical device, as taught by the present invention, could be implanted by injection using a syringe of sufficient size. It should also be appreciated that several devices can be implanted into the body to achieve the desired cell count necessary to remedy or reverse the ailment.

The semipermeable amphiphilic membrane employed to create the biological device of the present invention will be described with particular reference to the synthesis of amphiphilic networks from methacryloyl-capped polyisobutylene, the hydrophobic macromolecular monomer (MA-PIB-MA), and polyacrylates such as N,N-dimethyl acrylamide (DMAAm), N,N-dimethylaminoethyl methacrylate (DMAEMA), and 2-hydroxyethyl methyl-methacrylate (HEMA). The invention, however, should not be viewed as limited to these particular polyacrylates. This synthesis is similarly described in U.S. Pat. Nos. 4,942,204 and 5,073,381, which are incorporated herein by reference.

Starting materials for preparation of amphiphilic networks of this invention are (a) a hydrophobic acryloyl or meth acryloyl-capped polyolefin and (b) a hydrophilic ω (di-alkylamino) lower alkylacrylate or methacrylate or a hydrophilic dialkylacrylamide or methacrylamide or a hydrophilic ω hydroxy alkylacrylate or methacrylate.

The hydrophobic methacryloyl-capped polyolefin is a bifunctional macromolecular monomer or, more simply, a macromonomer which may be represented by the following formula (I)

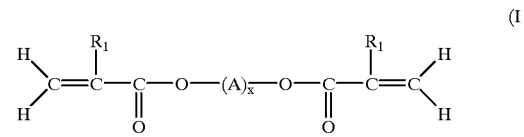

where A is a divalent unit derived from an olefin having four to about twelve carbon atoms or a mixture thereof and $R_1$ is hydrogen or methyl and x is the degree of polymerization of the macromonomer represented by formula (I).

The macromonomer (I) is a linear polyolefin having a number average molecular weight $M_n$ of at least about 500, preferably from about 2,000 to about 50,000, more preferably from about 4,000 to about 12,000; a degree of polymerization x corresponding to this $M_n$ (i.e. x is from about 25 to about 400) and molecular weight distribution $M_w/M_n$ from about 3.0 to about 1.1; capped at both ends with acryloyl or methacryloyl groups. Synthesis of the preferred macromonomer (I), i.e., methacryloyl-capped polyisobutylene is described in J. P. Kennedy and B Ivan, *Designed Polymers by Carbocationic Macromolecular Engineering, Theory and Practice*, Hanser Publishers, 1991, pages 168–170, 173–174, 178–179 and 193–197.

Other macromonomers of the formula (I) may be prepared by an analogous method, substituting acrylate for methacrylate ester and/or substituting another olefin having 4 to 12 carbon atoms, preferably another alpha mono-olefin such as 1-butene, 3-methyl-1-butene, styrene, etc., for isobutylene.

The hydrophilic comonomer segment is derived from a monofunctional monomer or mixture thereof that is copolymerizable with the acryloyl or methacryloyl and groups of the hydrophobic acryloyl- or methacryloyl-capped polyolefin and which yields a water soluble segment when homopolymerized. Preferred hydrophilic polyacrylate segments are those derived from acrylate monomer of formulas (II), (III), and (IV) as shown below:

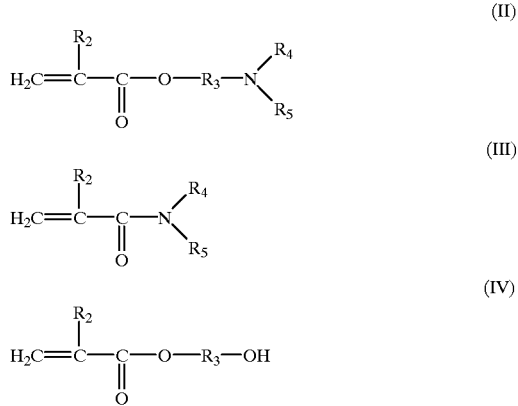

where $R^1$ is hydrogen or methyl, $R^3$ is an alkylene group of 2 to about 4 carbon atoms, and $R^4$ and $R^5$ may be the same or different and each is hydrogen or an alkyl radical of 1 to about 4 carbon atoms.

The preferred acrylate of the formula (II) is N,N-dimethylaminoethyl methacrylate (DMAEMA), the preferred acrylate of the formula (III) is N,N-dimethylacrylamide (DMAAm), and the preferred acrylate of formulas (IV) is 2-hydroxyethyl methacrylate (HEMA).

Other suitable hydrophilic comonomers include N-vinyl pyrrolidone, acrylamide and other similar hydrophilic acrylates or methacrylates.

Preferably the hydrophobic macromonomer (I) and the hydrophilic comonomer have the same ester group, which is preferably methacryloyl, so that the amphiphilic polymer network which is formed will be a random copolymer.

The weight ratio of hydrophobic macromonomer to hydrophilic comonomer is generally in the range of about 80:20 to about 20:80, preferably about 70:30 to about 30:70, most preferably from about 60:40 to about 40:60.

Copolymerization of the hydrophobic macromonomer with the hydrophilic comonomer is carried out under conventional free radical polymerization conditions, in a suitable organic solvent such as tetrahydrofuran, methylene chloride, benzene, or heptane at a temperature from about 40° to about 90° C., for a time sufficient to achieve the desired degree of cross-linking and to consume most or at least one of the two monomers (typically about 3 days at 60° C. will achieve the desired copolymerization), in the presence of a free radical initiator such as azobis (isobutylronitrile) (AIBN, cumyl peroxide, or tert-butylhydroperoxide. In the preferred embodiment, copolymerization of DMAAm or DMAEMA with MA-PIB-MA yields poly-N,N-dimethylacrylamide (PDMAAm) or poly-N,N-dimethylaminoethyl methacrylate (PDMAEMA) chains crosslinked by PIB chains. This reaction is shown in FIG. 1 which gives the preferred reactants, i.e., methacryloyl-capped polyisobutylene (MA-PIB-MA) (formula I-a) and dimethylaminoethyl methacrylate (DMAEMA (formula II-a) and the preferred initiator (AIBN) by way of example.

When the reaction is complete, the reaction product may be cooled to ambient temperature and may be extracted sequentially with a non-polar organic solvent (e.g., n-hexane), a polar organic solvent (e.g., ethanol) and water to remove unreacted hydrophilic macromonomer (e.g., MA-PIB-MA), unreacted hydrophilic comonomer (e.g., DMAEMA) and hydrophilic homopolymer (e.g., poly (dimethylaminoethyl)methacrylate homopolymer) which may be represented either as PDMAEMA or PMAEMA. This leaves an amphiphilic polymer network according to the invention, which consists of hydrophilic chains (e.g., PMAEMA) that are connected to hydrophobic chains (e.g., MA-PIB-MA). These points of connection are referred to as tri-functional crosslinking points that constitute the cross-linking agent. Differential scanning calorimetry (DSC) shows the existence of two glass transition temperatures in these networks, indicating a phase-separated domain structure.

With regard to the hydrophobic and/or hydrophilic content of the semipermeable membranes disclosed herein, it should be appreciated that the network content is a function of the amount of hydrophobic or hydrophilic monomer initially reacted in the copolymerization of the network. It has been found that the permeability and/or impermeability of the network is a function of the hydrophobic and/or hydrophilic content of the network. For example, it has been found that the permeability of the network will increase with increasing hydrophilic content. Likewise, it has been found that the permeability of the membrane will increase as the molecular weight of the hydrophobic macromonomer increases. Accordingly, the impermeability of the network can be increased by increasing the content of the hydrophobic macromonomer or decreasing the molecular weight of the hydrophobic macromonomer.

The use of the term permeability, as used herein, refers to the ability of molecules of a certain size to pass through the network. Thus, increasing permeability refers to the ability of the network to allow the passage of larger molecules. The membranes employed in the present invention can be synthesized to regulate the size of the molecules that pass therethrough by altering the hydrophobic/hydrophilic content of the network. It should be appreciated that with decreasing permeability, larger molecules are precluded from entering or exiting the reservoir. With respect to the molecular weight of such molecules that are precluded from defusing through the membrane, the membrane should generally be impermeable to those molecules having a molecular weight greater than about 100,000. This number is based on the premise that immunoproteins and the like have a molecular weight of greater than about 100,000. Of course, the membrane can be synthesized to preclude smaller molecules if such is desired. Accordingly, it is more preferred that the membrane preclude molecules having a molecular weight greater than about 80,000, and even more preferably those molecules having a molecular weight of greater than about 50,000. It should further be appreciated that although smaller molecules may still pass through such membranes, the rate at which such smaller molecules diffuse through the membrane is decreased as the membrane is synthesized to exclude smaller molecules.

It should also be appreciated that size characteristics are not the only criteria for determining permeability. For example, the geometric configuration of the molecules can impact their ability to permeate the membrane. It has, however, been found that effective immunoisolation can be achieved when the primary focus in synthesizing the membrane is directed towards permeability as a function of the size of the molecule.

To achieve a desired permeability, the hydrophobic content of the network is generally between about 40 to about 80 parts by weight based on a hundred parts by weight total network, which is the sum of the hydrophobic macromonomer and the hydrophilic polymerized monomer. Represented another way, the weight ratios of the hydrophilic to hydrophobic content within the network can be about 50 to about 50, or about 60 to about 40, of about 70 to about 30, depending on the permeability sought. Permeability is determined by experimentation as taught herein. In the preferred embodiment, where the semipermeable membrane employed is a biological device that encases pancreatic islet cells, the network can comprise from about 20 to about 60 parts by weight hydrophobic content, with the balance comprising hydrophilic content to total one hundred parts by weight, or preferably the hydrophobic content could comprise from about 30 to about 50 parts by weight, with a balance comprising hydrophilic content to total one hundred parts by weight.

The average molecular chain length M of the hydrophilic polymer chain (e.g., PDMAEMA) between two cross-linked sites may vary over a wide range, from about 1,000 and up, typically from about 1,200 to about 6,000, depending on the weight percentage of hydrophobic macromonomer units (e.g., MA-PIB-MA) in the network and the number average molecular weight $M_n$ of these macromonomer units. The molecular weight ($M_{n,hydrophobic}$) of the PIB segment of the preferred MA-PIB-MA can be determined by gel permeation chromatography (GPC) or H NMR spectroscopy of the MA-PIB-MA prior to copolymerization. The molecular weight of the hydrophilic segments between the crosslink points ($M_{c, hydrophilic}$), however, must be calculated. Thus, the overall compositions and hydrophilic/hydrophobic ratios can be readily determined. The $M_c$ value for hydrophobic chain increases with increasing $M_n$ value of the hydrophobic macromer and with decreasing weight ratio of hydrophobic macromer to hydrophilic monomer in the reactant charge. The $M_c$ values for hydrophilic polymer chains herein are calculated on the assumption that all of the hydrophobic macromer is incorporated into the amphiphilic polymer network, an assumption which is not always correct, particularly at higher hydrophobic macromer/hydrophilic monomer charge weight ratios. The average molecular chain length or $M_c$ value for the hydrophobic macromer is assumed to be the same as the $M_n$ value of the hydrophobic macromer.

Amphiphilic polymer networks of this invention are swellable in both water (and other polar solvents) and n-heptane (and other non-polar solvents), but are not soluble in either. Solvent swelling of the preferred networks MA-PIB-MA/PDMAEMA) ranges from about 170% to about 20% in water and from about 40% to about 170% in n-heptane with increasing MA-PIB-MA content. (The maxima and the minima indicate the percentage swelling in networks containing 48% and 71.5%, respectively of MA-PIB-MA.)

Networks according to this invention in which the hydrophobic macromonomer is based on an olefin other than isobutylene, and/or in which the hydrophilic polymer chains are based on a monomer other than DMAEMA, exhibit about the same swellability in both water and n-heptane as do the preferred amphiphilic polymer networks.

Tensile strength and elongation in amphiphilic networks of this invention are controllable. Tensile strength typically varies from about 35 $kg/cm^2$ to about 60 $kg/cm^2$ and elongation typically varies from about 160% to about 210%, the former decreasing and the latter increasing with increasing hydrophobic macromer content. By way of illustration, the preferred MA-PIB-MA/PDMAEMA networks exhibited tensile strength varying form 57.7 $kg/cm^2$ to 39.8 $kg/cm^2$ (at MA-PIB-MA contents of 48% and 71.5%, respectively) and elongation of 168% to 200% (also at MA-PIB-MA contents of 48% and 71.5%, respectively).

The synthesis of the semipermeable membranes of the present invention takes advantage of the technique of disguising one of the monomers so that the two monomers behave similarly in the polymerization medium to facilitate more efficient co-polymerization.

A monomer can be disguised by reacting either a hydrophobic or hydrophilic monomer with a removable blocking agent which essentially converts the monomer into its opposite. That is, a hydrophilic monomer can be converted into a hydrophobic monomer by reacting the monomer with an appropriate removable blocking agent, thereby allowing the blocked or disguised monomer to be reacted with a second hydrophobic monomer. Conversely, a hydrophobic monomer can be converted into a hydrophilic monomer by reacting the monomer with an appropriate removable blocking agent reacted with a hydrophilic monomer. Once the network is formed, the removable blocking agent can be removed by appropriate chemical methods yielding the desired amphiphilic network.

More generally, this process can be envisioned as a chemical transformation of a compatible, blocky, copolymer network into an amphiphilic network. This conversion or transformation can be affected by chemically converting or transforming one polymer block into a polymer block having opposite or near opposite solubility and/or compatibility properties. Thus, a blocky or somewhat blocky, copolymeric, compatible network can be transformed into an amphiphilic network by merely effecting a chemical transformation of one of the copolymer blocks into an incompatible derivative of the block.

The chemical transformation can be any chemical transformation that will affect the desired conversion or transformation of one segment of a polymer network into an incompatible derivative. One such transformation could be the protonation of a tertiary amine or amide which will convert a hydrophobic segment into a hydrophilic segment. The transformation can be, and preferably is accomplished on the network in a swollen state and thus can be thought of as quantitative derivatization of a compatible copolymeric network into an amphiphilic network.

The process comprises the steps of swelling a compatible, blocky, copolymeric, cross-linked network in a solvent and converting one block of said network into a block having opposite or nearly opposite compatibility properties whereby an amphiphilic network is formed. The compatible network can be of any form including a copolymer of a bifunctional macromonomer and a standard comonomer, two bifunctional macromonomers or two standard monomers and a cross-linking agent. The term "standard monomer" is used to refer to all typical monofunctional monomers such as acrylated, styrene and styrene derivatives, and all other polymerizable mono olefins and all polymerizable conjugated and non-conjugated diene monomers. Cross-linking agents include but are not limited to di and polyvinyl benzene and their derivatives, difunctional acrylates, and other similar cross-linking agents known in the art.

These procedures represent a significant improvement for manufacturing wider and more diverse types of amphiphilic networks from starting materials that are, or would be, in many respects, incompatible and chemically very different in behavior and response to different environments and thus, give rise to networks without amphiphilic characteristics or be unable to be copolymerized.

As an example of the blocking-deblocking process, HEMA (a hydrophilic methacrylate) can be converted to a hydrophobic methacrylate by reacting HEMA with the removable blocking agent trimethylsilyl chloride (TMSO-C1) to yield 2-(trimethylsiloxy)ethyl methacrylate (TMSHEMA).

Once the disguised HEMA has been prepared, the monomer can be reacted with the hydrophobic methacrylate capped polyisobutylene monomer (MA-PIB-MA) to yield a hydrophobic network which then can be swollen in a 5% hydrochloric acid 2-methoxyethanol solution which causes hydrolysis of the trimethylsiloxy group back to the hydroxy group. The hydrolysis converts the initially formed network into the desired amphiphilic network where the hydrophobic part of the network is represented by polyisobutylene and the hydrophilic part of the network is represented by HEMA. Thus, a hydrophilic monomer is converted into a hydrophobic monomer and polymerized with MA-PIB-MA to form a hydrophobic network which is then converted to an amphiphilic network by treating the swollen network with a deblocking agent. The deblocking agent can be any chemical reagent utilized by one of ordinary skill in the art of synthetic chemistry for reversibly converting a given monomer into a physically and chemically near opposite of itself.

This same process will work equally well by polymerizing a hydrophilic telechelic macromonomer with a disguised hydrophobic comonomer where the disguised hydrophobic comonomer is produced by blocking a hydrophobic monomer with a removable blocking agent which converts the hydrophobic monomer into a blocked monomer having hydrophilic characteristics. Thus, a hydrophilic macromonomer of formula (V)

$$Y\text{-PEO-Y} \qquad (V)$$

where Y is selected from the representative and illustrative group consisting of an acrylate, a methacrylate, a styryl group or other similar polymerizable group and where PEO represents a polyethyleneoxide segment having a molecular weight $M_n$ of at least about 200, preferably from about 2,000 to about 50,000, more preferably from about 4,000 to about 12,000, can be reacted with a salt form of N,N-dialky-4-vinyl benzylamide.

The salt for of N,N-dialkyl-4-vinyl benzylamide is easily made by treating the benzylamide with a strong acid such as Hcl, $H_2SO_4$, or other strong acids. Once the hydrophilic network is prepared, the network can be swollen in an appropriate hydrophilic solvent and treated with a base (the deblocking agent) such as an alkali hydroxide or other similar base which will convert the hydrophilic benzylamide salt into the hydrophobic benzylamide parent compound. Upon deblocking the hydrophilic network is converted into an amphiphilic network. Compounds of formula (V) can be readily prepared by reacting poly(ethylene glycol) of a desired $M_n$ with acryloyl chloride or other acrylate or methacrylate reagent used for preparing acrylate or methacrylate esters of the poly(ethylene glycol). This technique is well known in the art.

This technique can be generally applied to a wide variety of systems where the monomers have reactive groups that will allow them to be converted from their inherent either hydrophobic or hydrophilic state, into a disguised essentially opposite state. The conversion will make polymerization of the blocked monomer more efficient and effective with monomers that are chemically and physically similar to the disguised or blocked monomer.

It should be appreciated that, when carried out in the absence of a cross-linking agent, this disguising process requires one of the monomers to act as a cross-linking agent; for example, where MA-PIB-MA is both the hydrophobic monomer and cross-link agent. However, a blocked monomer and a second monomer can also be polymerized in the presence of a cross-linking agent to yield a cross-linked network. The only requirement in this latter system to insure the formation of an amphiphilic network, is that the polymerization would have to be blocky or somewhat blocky in nature. That is, copolymer segments of sufficient size would have to be produced during polymerization so that when deblocking occurs, the transformed network would show differential solubility and amphiphilic behavior could be expressed.

Furthermore, it should be appreciated that it is preferred, when synthesizing the membranes of employed in creating the biological devices of the present invention, that the hydrophobic and hydrophilic monomers must copolymerize in a random manner. This is achieved by selecting or disguising the monomers or macromers employed with similar polymerizable functionalities. Further, it is preferred that the kinetic chain of the hydrophilic monomer must be of sufficient length for the incorporation of at least two hydrophobic monomer units, i.e. MA-PIB-MA units, for crosslinking to occur. This is achieved by adjusting the concentration of the initiator, such as AIBN, according to the relationship generally represented by the formula $I/DP_n \sim \sqrt{[I]/[M]}$, where $DP_n$ is the number-average degree of polymerization, and [I] is the initiator concentration and [M] is the monomer concentration. The AIBN concentration decreases as the overall concentration of polymerizable groups decreases. It is still further preferred to avoid phase separation of the hydrophilic and hydrophobic monomers during copolymerization. This is best achieved by carrying out the crosslinking in THF solution, which is a good solvent for both polymers.

In order to demonstrate a practice of the present invention, the following examples have been prepared and tested as described in the Experimental section disclosed hereinbelow. The examples should not, however, be viewed as limiting the scope of the invention, as the claims serve to define the invention.

EXPERIMENTAL

Synthesis of PIB prepolymers was achieved as follows. A tert-Chlorine-telechelic PIB ($M_n$=4,500) and an allyl-telechelic PIB ($M_n$=10,000) with $M_w/M_n$=101–1.2 were prepared by living carbocationic polymerizations. The tert-chlorine ended PIB was quantitatively dehydrochlorinated with potassium tert-butoxide to —C(CH$_3$)=CH$_2$ endgroups. Both olefin-telechelic PIBs were then hydroborated with 9-BBN and oxidized with KOH/H$_2$O$_2$ to prepare primary hydroxyl termini. The hydroxyl-telechelic polymers were esterified with methacryloyl chloride to methacrylate-ditelechelic PIBs, MA-PIB-MA. The methodology used for the characterization of MA-PIB-MA prepolymers in terms of molecular weight, molecular weight distribution (by GPC) and MA endgroup concentration (by NMR spectroscopy) has been described hereinabove. A series of well-characterized ($M_n$, MWD, end-functionality $F_n$–2.0 ±0.1) MA-PIB-MAs have been copolymerized with a hydrophilic monomer, e.g., DMAAm or DMAEMA, by AIBN in THF solution to amphiphilic networks; THF is a common solvent for both PIB and the comonomers thereby yielding homogeneous reaction mixtures.

Table I displays the recipes used in synthesizing the semipermeable membranes employed in the present invention wherein the hydrophilic monomer is DMAAm. Table II likewise displays the recipes used in synthesizing the semipermeable membranes employed in the present invention wherein the hydrophilic monomer is DMAEMA. It should be understood that Mn(PIB) refers to the molecular weight of the polyisobutylene component of the hydrophobic macromonomer, and that the amount of hydrophobic and hydrophilic components reacted in the synthesis of the network is represented in both grams and moles.

inches in diameter and 1.0 inch in depth. The reaction mixture containing the comonomers plus AIBN have been dissolved in THF and poured in the teflon mold. The concentration of these solutions was adjusted such that after copolymerization they should yield membranes having about a 0.02 cm thickness. The filled mold was sealed by a teflon-coated rubber lid, placed in a press and the mold assembly heated to about 60° C. in an oven (DN-43H, Scientific Products) for 3 days. The mold with the cured products was removed from the oven, allowed to cool while sealed, opened, and the THF was allowed to evaporate. The products were carefully removed from the mold, exhaustively extracted in sequence with refluxing hexanes, methanol, and water to remove unreacted monomers and/or prepolymers. The overall composition of the extracted networks was determined gravimetrically and by infrared spectroscopy.

In order to demonstrate the ability of the semipermeable membranes employed to created the biological devices of the present invention to regulate the passage of biological matter, the following diffusion studies were performed. Specifically, experimentation was carried out to study the diffusion of glucose, insulin, and albumin through various amphiphilic networks prepared according to the teachings of the present invention.

The equipment assembled for the investigation of diffusion kinetics, was that which one of ordinary skill in the art could readily prepare. The apparatus simply included two chambers connected by an opening which could house a

TABLE I

| | | | | Ingredients | | |
|---|---|---|---|---|---|---|
| Example | Mn(PIB) | MA-PIB-MA (grams) | MA-PIB-MA (Mole × 10$^4$) | DMAAm (grams) | DMAAm (Mole × 10$^3$) | AIBN (Mole × 10$^5$) |
| 1 | 4,500 | 0.6 | 2.66 | 0.6 | 6.05 | 2.13 |
| 2 | 4,500 | 0.48 | 2.14 | 0.72 | 7.26 | 2.56 |
| 3 | 4,500 | 0.36 | 1.60 | 0.84 | 8.47 | 2.98 |
| 4 | 10,000 | 0.6 | 1.20 | 0.6 | 6.05 | 1.22 |
| 5 | 10,000 | 0.48 | 0.96 | 0.72 | 7.26 | 1.46 |

TABLE II

| | | | | Ingredients | | |
|---|---|---|---|---|---|---|
| Example | Mn(PIB) | MA-PIB-MA (grams) | MA-PIB-MA (Mole × 10$^4$) | DMAAm (grams) | DMAAm (Mole × 10$^3$) | AIBN (Mole × 10$^5$) |
| 6 | 4,500 | 0.6 | 2.66 | 0.6 | 3.82 | 1.34 |
| 7 | 4,500 | 0.48 | 2.14 | 0.72 | 4.58 | 1.58 |
| 8 | 4,500 | 0.36 | 1.60 | 0.84 | 5.34 | 1.89 |
| 9 | 10,000 | 0.6 | 1.20 | 0.6 | 3.82 | 0.79 |
| 10 | 10,000 | 0.48 | 0.96 | 0.72 | 4.58 | 0.91 |

Based on a review of the data in Tables I and II, it should be understood that when MA-PIB-MA, having a molecular weight of about 4500, was employed, the hydrophilic/hydrophobic weight ratios of the networks were about 50/50, 60/40, and 70/30. When MA-PIB-MA, having a molecular weight of about 10,000 was employed, the hydrophilic/hydrophobic weight ratios of the networks were about 50/50 and 60/40.

To synthesize the required thin membranes, copolymerizations were carried out in disk shaped teflon molds of 3.5 disc-shaped semipermeable membrane. The apparatus was thermostatically controlled. The thickness (δ) of the networks was determined by a thickness gauge (Randall & Stickney, Waltham, Mass.).

Known concentrations of glucose (2 mg/mL) and/or insulin (7 units/mL or 0.3 mg/mL) dissolved in phosphate buffer (pH 7.40) was placed in one chamber, and albumin (50 mg/mL) that was dissolved in phosphate buffer (pH 7.40) was placed in the other chamber. Samples were withdrawn as a function of time through the sampling ports and the concentrations of glucose, insulin and albumin were determined, respectively, by the o-toluidine condensation technique, radioimmunometric (coat-a-count) assay, and protein assay. Specifically, when o-toluidine is added under certain conditions to a system containing glucose, a green chromogen is formed whose concentration can be quantitated; the insulin concentration was determined by the National Reference Laboratory (Nashville, Tenn.) by radioimmunometric assay; and the albumin concentration was quantitated calorimetrically at 596 nm by the use of comassie green ethanol (95%) and phosphoric acid (85%).

The results of the above described diffusion studies are represented in Table III.

diffusion in a membrane may also exhibit a burst effect, i.e., when diffusion is initially fast and then it slows down as it approaches the steady state.

Also displayed in Table III are the diffusion coefficients (diffusivities) of glucose and insulin determined from the time to reach steady state. The following equation was used:

$$D = -(\delta^2/3t_B) = (\delta^2/6t_L)$$

where D is diffusion coefficient (cm$^2$/s), $\delta$ is thickness of the membrane, $t_B$ is the burst time and $t_L$ is the lag time; the latter two quantities have been obtained by extrapolating the amounts of solutes diffusing at steady state to the intercept on the time axis.

TABLE III

| Example | M$_o$, hydrophilic | Thickness($\delta$)(cm) | Permeability 1 × 10$^6$ (cm$^2$/s) | | | Diffusion Coefficient 1 × 10$^7$ (cm$^2$/s) | |
|---|---|---|---|---|---|---|---|
| | | | Glucose | Ensulin | Albumin | Glucose | Insulin |
| 1 | 2250 | 0.058 | 1.67 ± 0.03 | 0.11 ± 0.02 | 0 | 2.8 ± 0.2 | 0.11 ± 0.02 |
| 2 | 3375 | 0.028 | 2.03 ± 0.02 | 0.16 ± 0.02 | 0 | 5.2 ± 0.2 | 0.17 ± 0.02 |
| 3 | 5250 | 0.018 | 2.13 ± 0.04 | 0.31 ± 0.04 | 0 | 6.0 ± 0.3 | 0.23 ± 0.04 |
| 4 | 5000 | 0.024 | 1.92 ± 0.04 | 0.25 ± 0.03 | 0 | 0.38 ± 0.04 | 0.23 ± 0.02 |
| 5 | 7500 | 0.023 | 2.79 ± 0.06 | 0.44 ± 0.04 | 0 | 0.79 ± 0.03 | 0.30 ± 0.03 |
| 6 | 2250 | 0.081 | 1.35 ± 0.03 | 0.40 ± 0.03 | 0 | 5.4 ± 0.3 | 0.14 ± 0.03 |
| 7 | 3375 | 0.070 | 1.41 ± 0.02 | 0.51 ± 0.04 | 0 | 6.2 ± 0.2 | 0.23 ± 0.02 |
| 8 | 5250 | 0.086 | 1.67 ± 0.05 | 0.59 ± 0.02 | 0 | 7.5 ± 0.4 | 0.28 ± 0.02 |
| 9 | 5000 | 0.013 | 1.91 ± 0.04 | 0.38 ± 0.03 | 0 | 3.8 ± 0.3 | 0.11 ± 0.02 |
| 10 | 7500 | 0.017 | 2.21 ± 0.03 | 0.49 ± 0.04 | 0 | 8.0 ± 0.4 | 0.15 ± 0.02 |

Shown in TABLE III are the calculated molecular weights of the hydrophilic segments of the network, M$_{c,hydrophilic}$. The molecular weight of these hydrophilic segments in the network, which are situated between two hydrophobic crosslinking points, is calculated by $$M_{c,hydrophilic} = (W_h - M_n)/(2 W_{PIB})$$

where W$_h$ is the weight fraction of hydrophilic polymer, M$_n$ is the number average molecular weight of the PIB moiety (which is in fact the M$_c$ for the hydrophobic component), and W$_{PIB}$ is the weight fraction of PIB incorporated into the network.

The third column shows the measured thickness of the membranes. The next three columns indicate the permeabilities of glucose, insulin and albumin; the data represent averages of at least three experiments. Permeabilities (P) were determined in terms of the well-known equation $$(2AP/\delta V)t = -\ln(1 - 2C_t/C_o)$$

where P is permeability (cm$^2$/s), A is the surface area of the membrane (cm$^2$), $\delta$ is thickness of the membrane (cm), V is the chamber volume (cm$^3$), C$_t$ is the concentration of glucose or insulin in the receiving chamber at time t, C$_o$ is the concentration of glucose or insulin in the donor chamber; and t is time (sec). Permeabilities are obtained from the slope of $-\ln(2C_t/C_o)$ vs. t plots.

Figure 3:
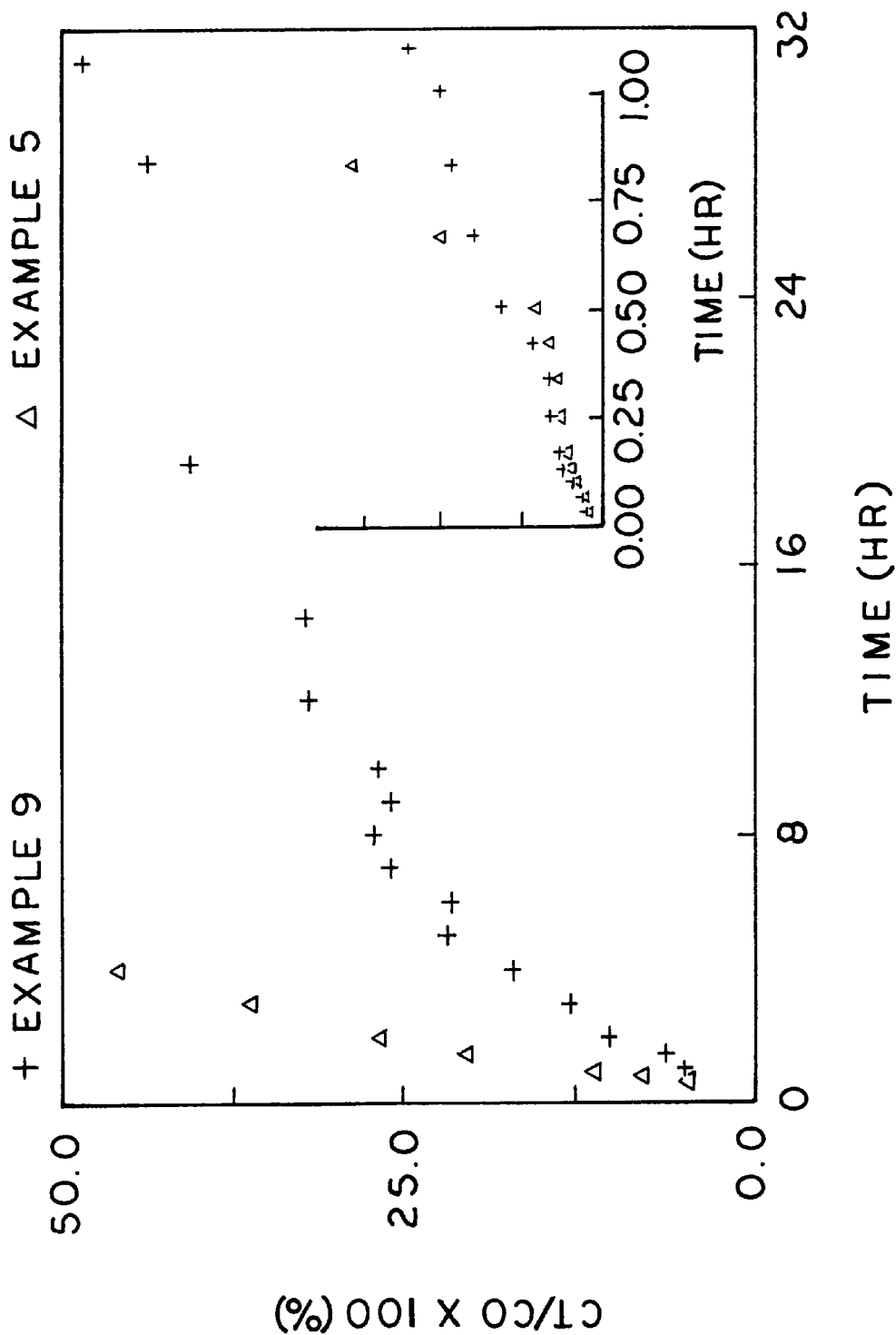
FIG. 3 is a is a plot of the raw diffusion data of Examples 5 and 9.

With reference to FIG. 3, raw diffusion data for two representative networks is displayed; namely Examples 5 and 9. Within FIG. 4 the corresponding linear plots are displayed, from which P was calculated. Similar plots were prepared for the other Examples listed in TABLE III. With particular regard to Example 5, the slow initial diffusion (see inset in FIG. 3) is due to the lag effect, which represents the time it takes for the membrane to get saturated and to reach steady state (zero-order) diffusion. The initial nonlinearity of Preliminary experiments using various membranes having an average thickness from about 0.013 to about 0.086 cm was run wherein single components were tested exclusively. In other words, only glucose, only insulin, or only albumin was placed in a chamber. These tests indicated that both glucose and insulin diffuse rapidly through the prepared membranes that were examined, and albumin was totally rejected within what is considered to be experimental accuracy, i.e., did not permeate the membrane. Data representative of such single component analysis is represented by the data gathered for Example 10 in TABLE III.

Subsequent experiments were carried out by simultaneous countercurrent diffusion. Examples 1–9 are representative of such tests. In these experiments the glucose and insulin were placed simultaneously in separate compartments, and the individual rates of their respective and countercurrent diffusions were determined. In these runs albumin was co-dissolved with glucose to mimic the effect of proteins in the blood serum on the rates. A comparison of the data obtained in the absence or presence of albumin shows that this protein does not affect the diffusion rates of glucose or insulin under our experimental conditions. Also, the permeabilities of glucose or insulin alone were very similar to those found in countercurrent experiments indicating that the diffusion of these biological molecules is independent of each other.

As should be evident from a review of the data in TABLE III, the permeability toward glucose seems to increase with increasing hydrophilic content and/or the molecular weight of the PIB. It is believed that the data for insulin will also indicate a similar trend.

Further experimentation was run employing the membrane of Example 5 wherein glucose and insulin concentrations placed into the diffusion chambers were consistent with those concentrations encountered within physiological environments. The following data and information was obtained: M$_{c,hydrophilic}$=7500; thickness=0.023 cm; Permeability at 1×10⁶ cm²/s for glucose, insulin and albumin was 2.74+/−0.04, 0.71+/−0.04, and 0, respectively. The diffusion coefficients at 1×10⁷ cm²/s for glucose and insulin was 0.77+/−0.04 and 0.78+/−0.03, respectively. It should be appreciated that the P values obtained for experimentation using physiological concentrations of glucose and insulin were similar to those using higher concentrations, within experimental variations. Thus, the permeabilities of both glucose and insulin appear to be high even at physiological concentrations. Within the accuracy of the method used it seems that albumin did not diffuse through any of the networks tested.

Indeed the P values of the amphiphilic membranes are about an order of magnitude higher than those reported for membranes of poly(2-hydroxyethyl methacrylate), porous poly(2-hydroxyethyl methacrylate), and dense polyurethane.

Thus it should be evident that the device and methods of the present invention are highly effective in encapsulating and immunoisolating cells. The invention is particularly suited for immunoisolating cells, but is not necessarily limited thereto. It should also be evident that the membranes employed in creating the biological devices of the present invention can be tailored to immunoisolate cells from a varying range of immuno-molecules, including those having smaller molecular weights.

Based upon the foregoing disclosure, it should now be apparent that the use of the biological devices described herein will carry out the objects set forth hereinabove. It is, therefore, to be understood that any variations evident fall within the scope of the claimed invention and thus, the selection of specific component elements can be determined without departing from the spirit of the invention herein disclosed and described. In particular, devices according to the present invention are not necessarily limited to those having a cells disclosed herein or those that treat ailments disclosed herein. Thus, the scope of the invention shall include all modifications and variations that may fall within the scope of the attached claims.

What is claimed is:

1. A semipermeable biological implant comprising:

a semipermeable polymeric network formed into a geometric shape having an inner volume, said implant having cells encapsulated within said inner volume and capable of immununoisolating said encapsulated cells when said inplant is implanted into a biological medium, said semipermeable polymer network comprising the polymerization product of acryloyl or methacryoyl capped polyisobutylene and mixtures thereof, wherein said polyisobutylene is formed by cationic polymerization, and a hydrophilic segment derived from an acrylate selected from the group consisting of formulas (II), (III) and (IV)

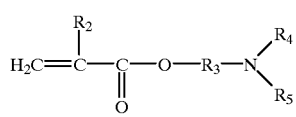 (II)

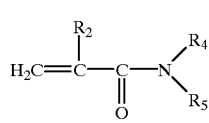 (III)

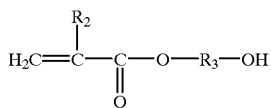 (IV)

where $R_2$ is hydrogen or methyl, $R_3$ is an alkylene group having from about 2 to about 4 carbon atoms, and $R_4$ and $R_5$ may be the same or different and are selected from the group consisting of hydrogen and alkyl groups having from 1 to about 4 carbon atoms;

wherein the ratio of capped polyisobutylene to said hydrophilic segments is from about 50:50 parts by weight to about 30:70 parts by weight; and wherein the polymeric network allows the passage of glucose and insulin and prevents the passage of molecules having a molecular weight of greater than 50,000 daltons.

2. A method of encapsulating cells within the inner volume of a geometric shape and immunoisolating cells from a biological medium comprising the steps of:

forming a semipermeable amiphiphilic copolymer network by reacting acryloyl-capped or methacryoyl-capped polyisotbutyiene, wherein said polyisobutylene is prepared by cationic polymerization, with hydrophilic segments derived from an acrylate selected from the group consisting of formulas (II), (III) and (IV)

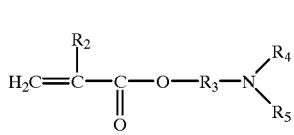 (II)

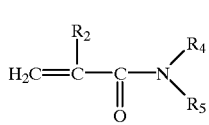 (III)

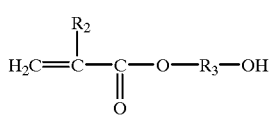 (IV)

where $R_2$ is hydrogen or methyl, $R_3$ is ail alkylene group having from about 2 to about 4 carbon atoms, and $R_4$ and $R_5$ may be the same or different and are selected from the group consisting of hydrogen and alkyl groups having from 1 to about 4 carbon atoms;

wherein the ratio of capped polyisobutylene to said hydrophilic segments is from about 50:50 parts by weight to about 30:70 parts by weight; and wherein the semipermeable copolymer network allows the passage of glucose and insulin, and where said membrane prevents the passage of molecules having a molecular weight of greater than 50,000 daltons;

forming the semipermeable copolymer network into a geometric shape having an inner volume;

placing cells within the inner volume of said geometric shape;

sealing said geometric shape containing said cells, thereby encapsulating said cells within the inner volume of said geometric shape; and implanting said geometric shape having cells encapsulated therein into a biological medium.

3. The biological implant of claim 1 wherein the geometric shape is an elongated tube.

4. The biological implant of claim 3 wherein the length of said elongated tube is less than about 20 cm.

5. The biological implant of claim 4 wherein the length of said elongated tube is less than about 10 cm.

6. The biological implant of claim 5 wherein the length of said elongated tube is about 2 cm to about 5 cm.

7. The biological implant of claim 3 wherein the inner diameter of said elongated tube is less than about 3 mm.

8. The biological implant of claim 7 wherein the inner diameter of said elongated tube is less than about 2 mm.

9. The biological implant of claim 8 wherein the inner diameter of said elongated tube is less than about 1 mm.

10. The biological implant of claim 3 wherein the inner volume of said elongated tube is less than about 1 ml.

11. The biological implant of claim 9 wherein the inner volume of said elongated tube is less than about 0.5 ml.

12. The biological implant, as set forth in claim 1 wherein said cells include pancreatic islet cells.

13. The biological implant, as set forth in claim 1 wherein said amphiphilic copolymer network membrane does not allow the passage of molecules having a molecular weight of greater than about 100,000 daltons.

14. The biological implant, as set forth in claim 1 wherein said polyisobutylene is formed by cationic polymerization.

15. The biological implant, as set forth in claim 1 wherein said cells include pancreatic islet cells.

16. The biological implant, as set forth in claim 1 wherein said polyisobutylene is formed by cationic polymerization.

17. The biological implant, as set forth in claim 1 wherein said polyisobutylene has a molecular weight of about 4,500.

18. The biological implant, as set forth in claim 1 wherein said polyisobutylene has a molecular weight of about 10,000.

19. The biological implant, as set forth in claim 1 wherein said polyisobutylene is methacryloyl capped.

20. The biological implant, as set forth in claim 1 wherein said amphiphilic copolymer network comprises about 50 parts by weight of said polyisobutylene and about 50 parts by weight of said hydrophilic segment.

21. The biological implant, as set forth in claim 1 wherein said amphiphilic copolymer network comprises about 40 parts by weight of said polyisobutylene and about 60 parts by weight of said hydrophilic segment.

22. The biological implant, as set forth in claim 1 wherein said amphiphilic copolymer network comprises about 30 parts by weight of said polyisobutylene and about 70 parts by weight of said hydrophilic segment.

* * * * *